(12) United States Patent
Guo et al.

(10) Patent No.: US 10,359,374 B2
(45) Date of Patent: Jul. 23, 2019

(54) IDENTIFICATION OF ANNULUS MATERIALS USING FORMATION POROSITY

(71) Applicant: HALLIBURTON ENERGY SERVICES, INC., Houston, TX (US)

(72) Inventors: Qingzhen Guo, Humble, TX (US); James Galford, Missouri City, TX (US); Weijun Guo, Houston, TX (US)

(73) Assignee: Halliburton Energy Services, Inc., Houston, TX (US)

(*) Notice: Subject to any disclaimer, the term of this patent is extended or adjusted under 35 U.S.C. 154(b) by 44 days.

(21) Appl. No.: 15/532,039

(22) PCT Filed: Apr. 19, 2016

(86) PCT No.: PCT/US2016/028306
§ 371 (c)(1),
(2) Date: May 31, 2017

(87) PCT Pub. No.: WO2017/184125
PCT Pub. Date: Oct. 26, 2017

(65) Prior Publication Data
US 2018/0195980 A1    Jul. 12, 2018

(51) Int. Cl.
*G01V 5/10* (2006.01)
*G01N 23/05* (2006.01)
*G01N 29/265* (2006.01)
*G01N 21/53* (2006.01)
*G01N 33/38* (2006.01)
*E21B 47/12* (2012.01)

(52) U.S. Cl.
CPC ........... *G01N 23/05* (2013.01); *G01N 21/532* (2013.01); *G01N 29/265* (2013.01); *G01N 33/383* (2013.01); *E21B 47/124* (2013.01); *G01V 5/10* (2013.01)

(58) Field of Classification Search
CPC .... G01N 23/05; G01N 21/532; G01N 29/265; G01N 33/303
See application file for complete search history.

(56) References Cited

U.S. PATENT DOCUMENTS

| | | | |
|---|---|---|---|
| 3,815,677 A | | 6/1974 | Pennebaker, Jr. |
| 4,506,156 A | * | 3/1985 | Mougne ................ G01V 5/101 250/266 |
| 5,461,909 A | * | 10/1995 | Arnold ............... E21B 47/1015 250/255 |

(Continued)

OTHER PUBLICATIONS

Lee, Hun Gil, PCT Search Report for PCT Application No. PCT/US2016/028306 dated Jan. 16, 2017.

(Continued)

*Primary Examiner* — David P Porta
*Assistant Examiner* — Djura Malevic
(74) *Attorney, Agent, or Firm* — Locke Lord LLP

(57) ABSTRACT

Methods, systems, and computer program products for identifying annular space materials calculate a near-to-far ("N/F") neutron count ratio from neutron count rates detected by detectors located near to and far from a neutron source, respectively. The N/F neutron count ratio may then be used along with formation porosity to provide an estimation of the type of material that may be present in the annular space.

14 Claims, 8 Drawing Sheets

(56) References Cited

U.S. PATENT DOCUMENTS

| | | | | |
|---|---|---|---|---|
| 5,581,079 | A * | 12/1996 | Mickael | G01T 3/00 250/269.4 |
| 5,699,246 | A * | 12/1997 | Plasek | E21B 47/00 175/50 |
| 6,032,102 | A * | 2/2000 | Wijeyesekera | G01V 5/107 702/8 |
| 6,173,606 | B1 * | 1/2001 | Mosley | E21B 47/0005 166/253.1 |
| 8,964,504 | B2 * | 2/2015 | Chace | G01V 5/101 250/269.4 |
| 9,031,790 | B2 * | 5/2015 | Thornton | G01V 5/107 250/265 |
| 9,696,454 | B1 * | 7/2017 | Gade | G01V 5/102 |
| 9,863,895 | B1 * | 1/2018 | Ma | G01N 23/025 |
| 9,890,632 | B2 * | 2/2018 | Ma | E21B 47/12 |
| 2008/0112262 | A1 * | 5/2008 | Tang | E21B 47/0005 367/35 |
| 2009/0086575 | A1 * | 4/2009 | Tello | E21B 47/0005 367/35 |
| 2011/0001040 | A1 * | 1/2011 | Smith, Jr. | G01V 5/101 250/264 |
| 2011/0238313 | A1 * | 9/2011 | Thornton | G01V 5/107 702/8 |
| 2012/0043459 | A1 * | 2/2012 | Hill | E21B 23/08 250/269.4 |
| 2012/0075953 | A1 * | 3/2012 | Chace | E21B 47/0005 367/35 |
| 2013/0062057 | A1 * | 3/2013 | Smith, Jr. | E21B 47/00 166/254.2 |
| 2013/0345983 | A1 * | 12/2013 | Guo | G01V 5/104 702/8 |
| 2015/0234084 | A1 * | 8/2015 | Thornton | G01V 5/107 250/262 |
| 2016/0202387 | A1 * | 7/2016 | Fox | E21B 47/0005 73/152.58 |
| 2016/0326865 | A1 * | 11/2016 | Zhang | G01V 5/06 |
| 2017/0192122 | A1 * | 7/2017 | Gade | G01V 5/102 |

OTHER PUBLICATIONS

Lee, Hun Gil, PCT Written Opinion for PCT Application No. PCT/US2016/028306 dated Jan. 16, 2017.

* cited by examiner

IDENTIFICATION OF ANNULUS MATERIALS USING FORMATION POROSITY

TECHNICAL FIELD

The exemplary embodiments disclosed herein relate generally to systems and method for evaluating materials within an annular space between a well casing and a subterranean formation or between two well casings. In particular, the embodiments disclosed herein relate to systems and method for identifying such materials using the formation's neutron count ratio and porosity.

BACKGROUND

In many oil wells, the annular space or annulus between the well casing or liner and the subterranean formation is filled with cement. The cement protects the oil and/or gas-producing zones surrounding the casing from contamination by subterranean brine and helps prevent corrosion of the casing or liner by other corrosive fluids and electrolysis. Cementing also helps protect any fresh water-containing strata from contamination by the brine or by petroleum fluids that could otherwise travel in the wellbore annulus. Additional benefits of cementing include bonding of the well casing to the formation or to other well casings to support any vertical and radial loads applied to the casings. For at least these reasons, it is useful to be able to determine whether there is cement in the annular space and the quality of the cement, or whether there is some other material, such as barite, air, or the like filling the annular space.

Cement quality evaluations are traditionally conducted downhole by running cement bond logging (CBL) tools in a cased wellbore. Other evaluation methods include running an open hole sonic log and cased hole neutron log to detect fluid channels in the cement. The cased hole neutron log typically requires information regarding the porosity of the formation, as porosity may affect how easily neutrons travel through the formation to the detectors. The open and cased hole logs, hole dimensions, and related information are then provided as input to a mathematical model generated on a computer to determine a volume of fluid filled channels in the cement sheath and estimate the cement integrity based on the fluid filled channel volume.

Other techniques exist for evaluating the materials within the annular space between a well casing and a subterranean formation or between two well casings. Nevertheless, a need exists for an improved way for evaluating such annulus materials.

BRIEF DESCRIPTION OF THE DRAWINGS

For a more complete understanding of the exemplary disclosed embodiments, and for further advantages thereof, reference is now made to the following description taken in conjunction with the accompanying drawings wherein.

DESCRIPTION OF EXEMPLARY EMBODIMENTS

The following discussion is presented to enable a person skilled in the art to make and use the exemplary disclosed embodiments. Various modifications will be readily apparent to those skilled in the art, and the general principles described herein may be applied to embodiments and applications other than those detailed below without departing from the spirit and scope of the disclosed embodiments as defined herein. Accordingly, the disclosed embodiments are not intended to be limited to the particular embodiments shown, but are to be accorded the widest scope consistent with the principles and features disclosed herein.

As alluded to above, the embodiments disclosed herein relate to a method and system for identifying annular space materials using formation neutron count ratios and porosities. The disclosed embodiments advantageously employ existing neutron logging tools, including existing neutron sources and neutron detectors to identify annular space materials. More specifically, the disclosed embodiments position at least one neutron detector on the logging tool proximal or near to the neutron source and at least one neutron detector distal or far from the neutron source. The disclosed embodiments thereafter calculate a near-to-far ("N/F") neutron count ratio from the neutron count rates detected by the near and far neutron detectors. The N/F neutron count ratio may then be used along with formation porosity to provide an estimation of the type of material that may be present in the annular space.

Figure 1:
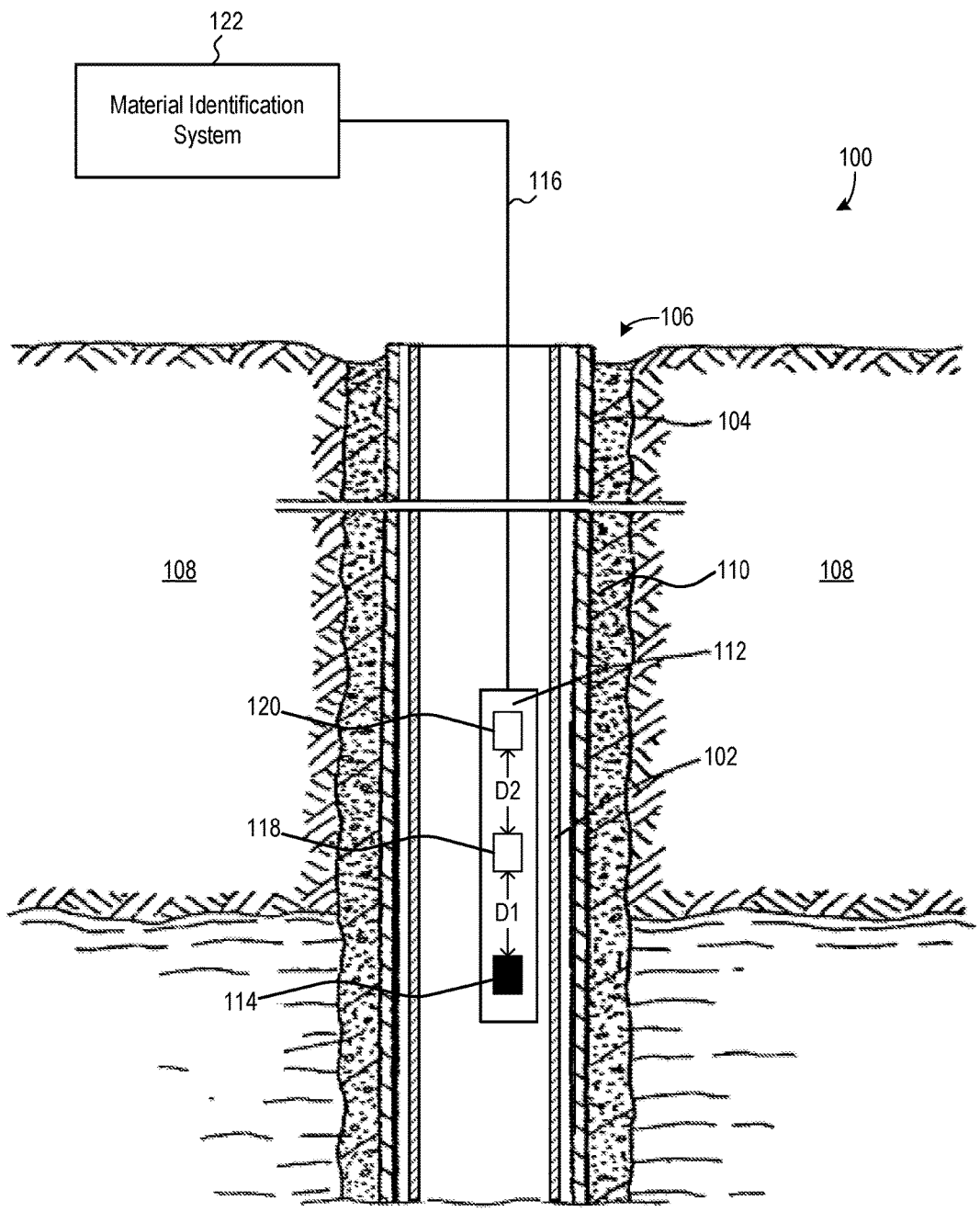
FIG. 1 illustrates an exemplary well in which an annulus material identification tool may be used according to the disclosed embodiments.

Referring now to FIG. 1, a section of a well 100 is shown for producing hydrocarbon in which one or more of the embodiments disclosed herein may be employed. The well 100 may be any type of well where casing is needed, including offshore, onshore, vertical, horizontal, deviated, and in any type of subterranean formation. The particular well 100 depicted here includes a tubing 102 and at least one casing 104 that defines an annular space 106 between the casing and the formation 108. The annular space 106 is typically filled with one or more types of material 110, such as cement, barite, air, or the like, at various sections along the length of the well 100.

Information regarding the type of material 110 and the extent to which the material fills the annular space 106 is important in a number of oilfield operations. For example, when planning a retrieval operation for the casing 104, it is useful to know whether cement, barite, air, or some other material is present in the annular space 106. To this end, a neutron logging tool 112 having a neutron source 114 coupled thereto may be lowered into the well 100 (e.g., down the tubing 102) to facilitate identification of the material 110 in the annular space 106. The neutron logging tool 112 may be lowered into the well 100, for example, by a wireline 116 or other suitable conveyance, such as a slickline, coiled tubing, a drill string, downhole tractor, and the like.

In accordance with the disclosed embodiments, the neutron logging tool 112 may have at least one neutron detector 118 positioned lengthwise near to the neutron source 114 and at least one neutron detector 120 positioned lengthwise far from the neutron source 114. These neutron detectors 118, 120 may be any suitable neutron detectors known to those having ordinary skill in the art, including helium-3 (He-3) proportional counters and the like. Similarly, the neutron source 114 may be any suitable neutron source, including plutonium-beryllium (Pu—Be), americium-beryllium (Am—Be), californium-252 (Cf-252), or deuterium-tritium (D-T) neutron sources. The distance D1 lengthwise from the neutron source 114 to the near detector 118 and the distance D2 lengthwise from the near detector 118 to the far detector 120 may be selected as needed for optimal effect depending on the length of the neutron logging tool 112.

The neutron count rates (counts/seconds) detected by the neutron detectors 118, 120 may then be communicated to a material identification system 122 located either at the surface of the formation 108 proximate to the well 100 (i.e., for near real-time in-situ processing) or at another remote facility. A suitable telemetry unit (not expressly shown) connected to the neutron logging tool 112 may be used to communicate the neutron count rates to the material identification system 122. It is also possible to locate the material identification system 122 or a portion thereof in the neutron logging tool 112 itself for near real-time in-situ identification of the material 110. The material identification system 122 may then use the neutron count rates detected by the neutron detectors 118, 120 to calculate a N/F neutron count ratio for the well 100. The N/F neutron count ratio may then be used along with the formation porosity to provide an estimation of the type of material 110 that may be present in the annular space 106, as discussed further herein.

Figure 2:
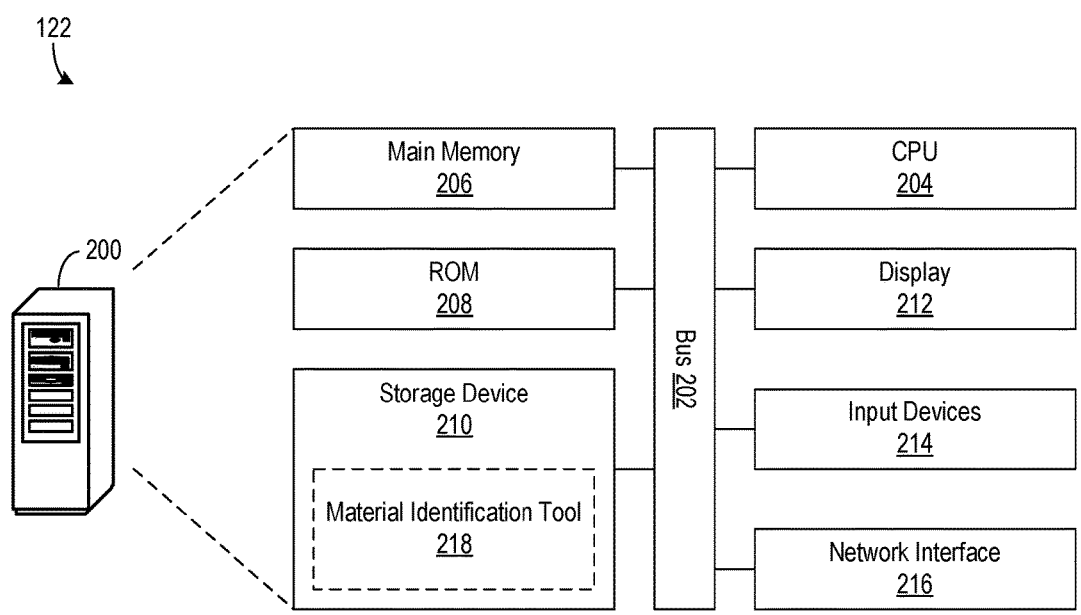
FIG. 2 illustrates an exemplary system that may be used to run the material identification tool according to the disclosed embodiments.

FIG. 2 illustrates an exemplary implementation of the material identification system 122 according to the embodiments disclosed herein. In general, the material identification system 122 may include a computing system, such as a workstation, desktop, or laptop computer, indicated at 200, or it may include a custom computing system developed for a particular application. In a typical arrangement, the computing system 200 includes a bus 202 or other communication pathway for transferring information among other components within the computing system 200, and a CPU 204 coupled with the bus 202 for processing the information. The computing system 200 may also include a main memory 206, such as a random access memory (RAM) or other dynamic storage device coupled to the bus 202 for storing computer-readable instructions to be executed by the CPU 204. The main memory 206 may also be used for storing temporary variables or other intermediate information during execution of the instructions by the CPU 204.

The computing system 200 may further include a read-only memory (ROM) 208 or other static storage device coupled to the bus 202 for storing static information and instructions for the CPU 204. A computer-readable storage device 210, such as a nonvolatile memory (e.g., Flash memory) drive or magnetic disk, may be coupled to the bus 202 for storing information and instructions for the CPU 204. The CPU 204 may also be coupled via the bus 202 to a display 212 for displaying information to a user. One or more input devices 214, including alphanumeric and other keyboards, mouse, trackball, cursor direction keys, and so forth, may be coupled to the bus 202 for transferring information and command selections to the CPU 204. A communications interface 216 may be provided for allowing the computing system 200 to communicate with an external system or network.

The term "computer-readable instructions" as used above refers to any instructions that may be performed by the CPU 204 and/or other components. Similarly, the term "computer-readable medium" refers to any storage medium that may be used to store the computer-readable instructions. Such a medium may take many forms, including, but not limited to, non-volatile media, volatile media, and transmission media. Non-volatile media may include, for example, optical or magnetic disks, such as the storage device 210. Volatile media may include dynamic memory, such as main memory 206. Transmission media may include coaxial cables, copper wire and fiber optics, including the wires of the bus 202. Transmission itself may take the form of electromagnetic, acoustic or light waves, such as those generated for radio frequency (RF) and infrared (IR) data communications. Common forms of computer-readable media may include, for example, magnetic medium, optical medium, memory chip, and any other medium from which a computer can read.

In accordance with the disclosed embodiments, a material identification tool 218, or the computer-readable instructions therefor, may also reside on or be downloaded to the storage device 210 for execution. The material identification tool 218 may be a standalone tool or it may be part of a larger suite of tools that may be used to obtain an overall evaluation of the well 100. Such an identification tool 218 may be implemented in any suitable computer programming language or software development package known to those having ordinary skill in the art, including various versions of C, C++, FORTRAN, and the like. Users may then use the material identification tool 218 to obtain an estimation of the type of material 110 that may be present in the annular space 106.

Figure 3:
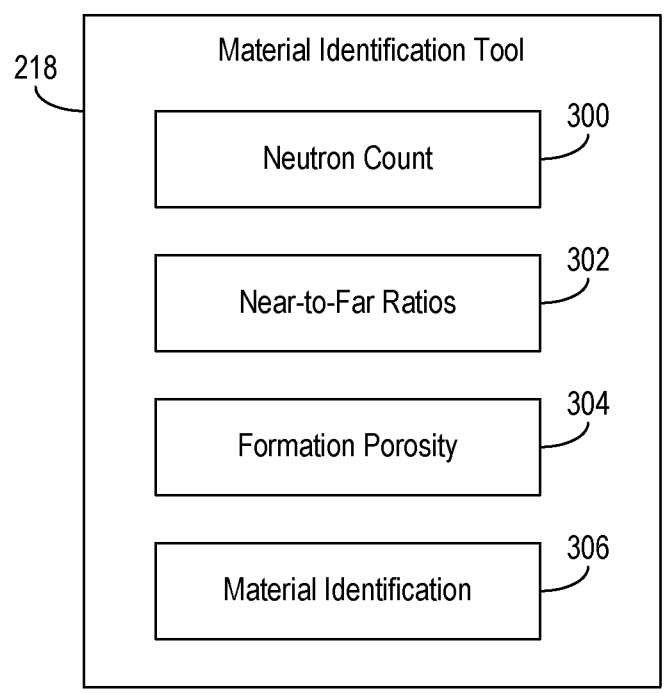
FIG. 3 illustrates an exemplary material identification tool according to the disclosed embodiments.

An exemplary implementation of the material identification tool 218 is depicted in FIG. 3. As FIG. 3 shows, the tool 218 has a number of functional components, including a neutron count component 300, a N/F ratio component 302, a formation porosity component 304, and a material identification component 306. Note that although the various components 300-306 are depicted here as discrete blocks, it should be understood that any block may be divided into two or more constituent blocks and that two or more blocks may be combined to form a single block without departing from the scope of the exemplary disclosed embodiments.

In general operation, the neutron count component 300 is primarily responsible for obtaining or otherwise acquiring the neutron count rates detected by the detectors 118, 120, either in real time or on a delayed basis. In some embodiments, the neutron count rates may be beneficially obtained in conjunction with a conventional neutron logging operation (e.g., a cased hole neutron log). This entails using the same neutron source 114 both for identification of the material 110 and for the conventional neutron logging operation. Indeed, the same neutron count rates detected by either or both of the neutron detectors 118, 120 for material identification purposes may also be used for conventional neutron logging purposes in some embodiments. Alternatively, the neutron detectors 118, 120 may be used to detect the neutron count rates independently of any conventional neutron logging operation, but with the same neutron source 114 as the conventional neutron logging operation.

Once the neutron count rates are acquired, the neutron count component 300 provides these neutron count rates, or data representing same, to the N/F ratio component 302. This component is primarily responsible for calculating a N/F neutron count ratio for the well 100 using the neutron count rates. N/F neutron count ratios have certain advantages over other types of indicators in that these ratios differ greatly and consistently depending on whether cement, barite, or air is present in the annular space 106, as shown later herein, owing to each material's significantly different neutron slow-down parameters. In some embodiments, the N/F ratio component 302 may calculate the N/F neutron count ratio using Equation (1) below or suitable variations thereof:

$$N/F = \frac{\text{Near Detector Neutron Count Rate}}{\text{Far Detector Neutron Count Rate}} \quad (1)$$

As for the formation porosity component 304, this component is primarily responsible for obtaining information regarding the porosity of the formation 108. As mentioned earlier, formation porosity necessarily affects the neutron count rates and therefore the N/F neutron count ratios may vary depending on the formation porosity. Such porosity information is typically readily available from survey data and other data previously obtained for the well 100, but the porosity information may also be obtained using the neutron logging tool 112 itself and the neutron detectors 118, 120 in real time if needed. The porosity information may then be used together with the N/F neutron count ratio to provide an estimation of the type of material 110 in the annular space 106.

The material identification component 306 is primarily responsible for estimating the type of material 110 in the annular space 106 using the N/F neutron count ratio and the formation porosity obtained above. In some embodiments, the material identification component 306 may estimate the type of material 110 by comparing the N/F neutron count ratio obtained above to either known or simulated N/F neutron count ratios for a reference case. Where the reference case is a simulated case, the simulation may be performed with Monte Carlo neutron photon simulators or other suitable nuclear transport simulators. Thereafter, if the N/F neutron count ratio obtained above is substantially the same (e.g., within ±10%) as one of the N/F neutron count ratios for the reference case, then the material identification component 306 may indicate that the material 110 is substantially the same as one of the materials in the reference case. Otherwise, the material identification component 306 may indicate that further investigation and/or interpretation may be needed.

Figure 4:
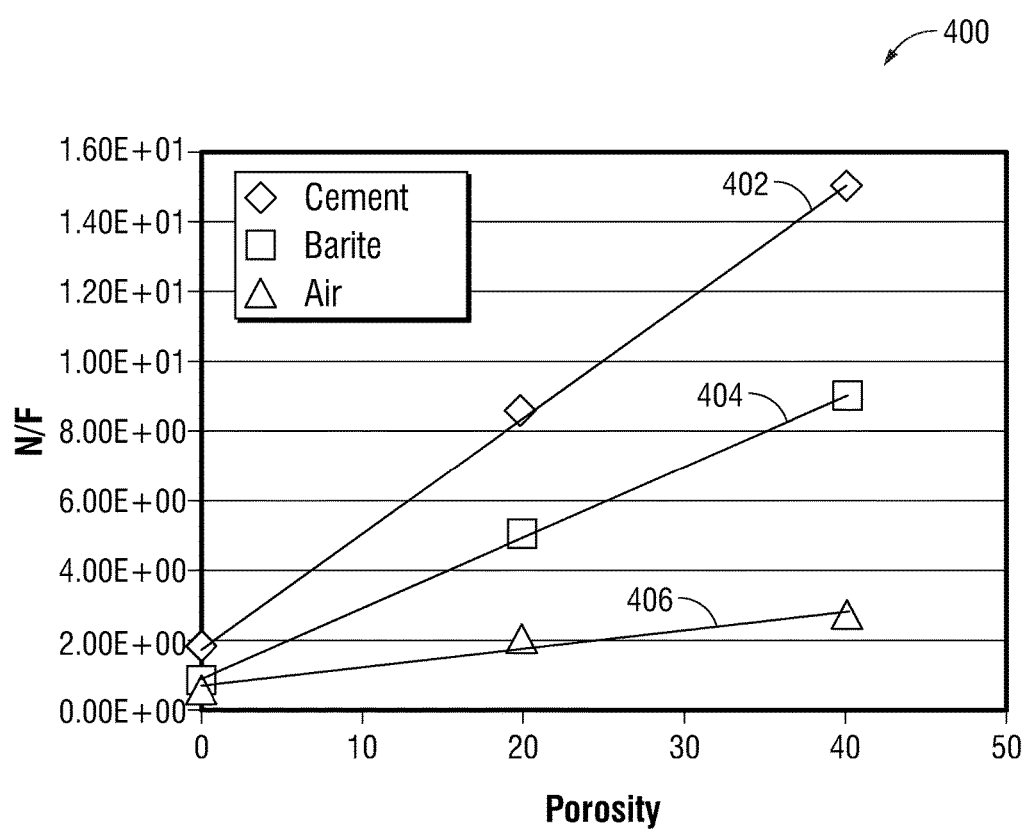
FIG. 4 illustrates exemplary neutron near-to-far ratios for materials in the annular space of a well according to the disclosed embodiments.

Referring now to FIG. 4, an exemplary plot 400 for a simulated reference case that may be used with the material identification tool 218 is shown. In this exemplary plot 400, the vertical axis represents N/F neutron count ratios while the horizontal axis represents formation porosities. The plot 400 includes several curves representing simulated N/F neutron count ratios for several different types of materials 110. The curve labeled 402 represents N/F neutron count ratios for cement at various formation porosities, the curve labeled 404 represents N/F neutron count ratios for barite at various formation porosities, and the curve labeled 406 represents N/F neutron count ratios for air at various formation porosities. For this reference case, the simulated annular space measures about 1.25 inches thick, the simulated cement is type "H," and the simulated temperature is about 60° F.

As can be seen in FIG. 4, each of the curves 402, 404, 406 representing the different materials is uniquely identifiable from the other curves 402, 404, 406 over a wide range of formation porosities (e.g., 0, 20, and 40). Thus, if the N/F neutron count ratio calculated by the material identification tool 218 substantially coincides (e.g., within ±10%) with one of the curves 402, 404, 406, then there is a high degree of confidence that the material 110 in the annular space 106 (see FIG. 1) resulting in the calculated ratio is substantially the same as the material represented by such curve 402, 404, 406. Otherwise, the material identification tool 218 may indicate that additional investigation and/or interpretation is needed.

Figure 5:
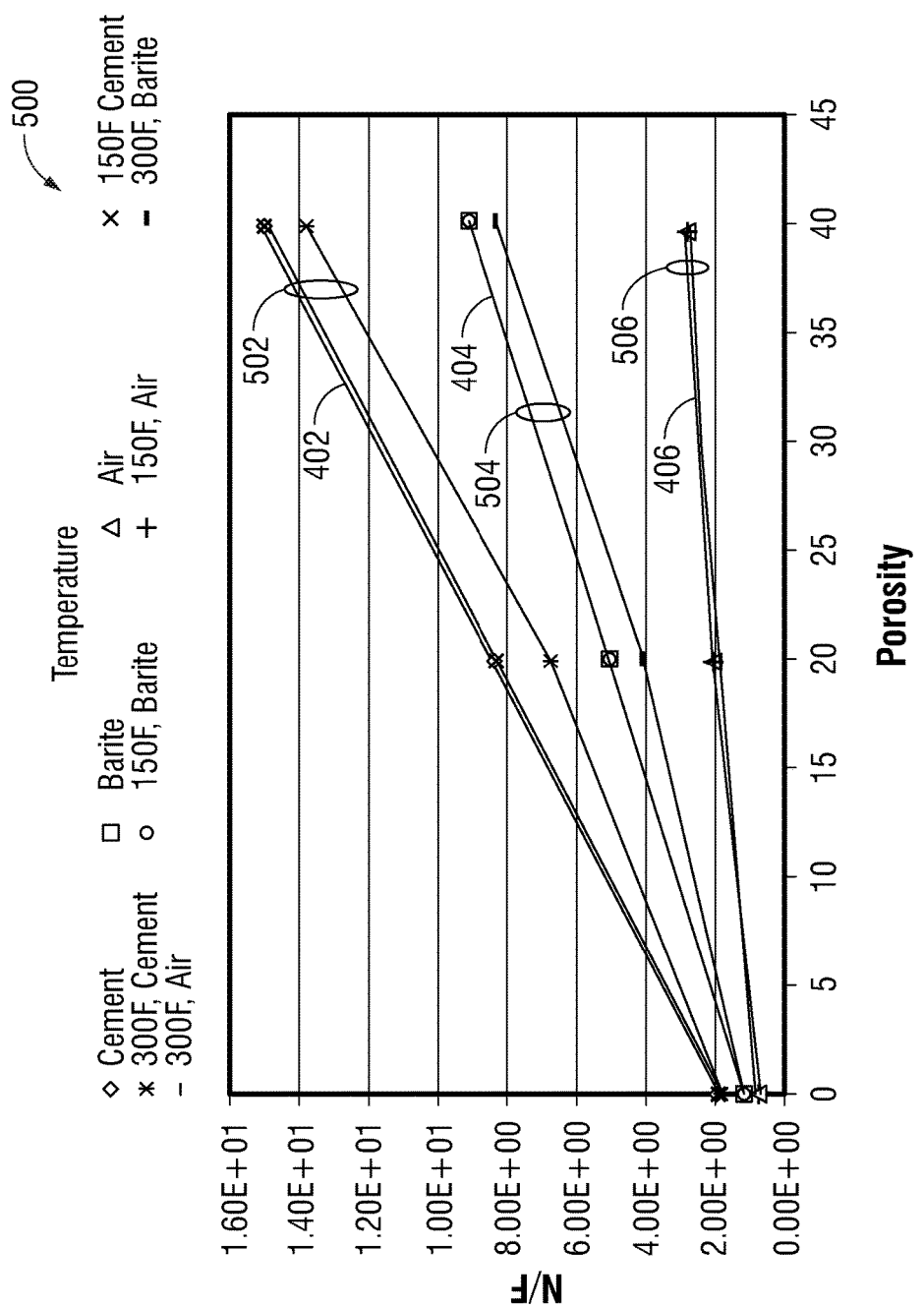
FIG. 5 illustrates exemplary neutron near-to-far ratios for materials in the annular space of another well according to the disclosed embodiments.

Referring next to FIG. 5, the above N/F neutron count ratio curves 402, 404, 406 for the different materials remain uniquely identifiable even over a wide range of temperatures. In FIG. 5, an exemplary plot 500 showing the same N/F neutron count ratio curve 402, 404, 406 from FIG. 4 (i.e., cement type "H," temperature about 60° F.) has been overlaid with data representing the same three materials, but at 150° F. and 300° F., respectively. Because some of the data is clustered so closely, none of the curves representing the higher temperatures have been separately labeled for ease of viewing. Nevertheless, as can be seen, the N/F neutron count ratios for cement, barite, and air at the higher temperatures respectively remain uniquely identifiable from one another, assuming other downhole conditions stay the same.

Figure 6:
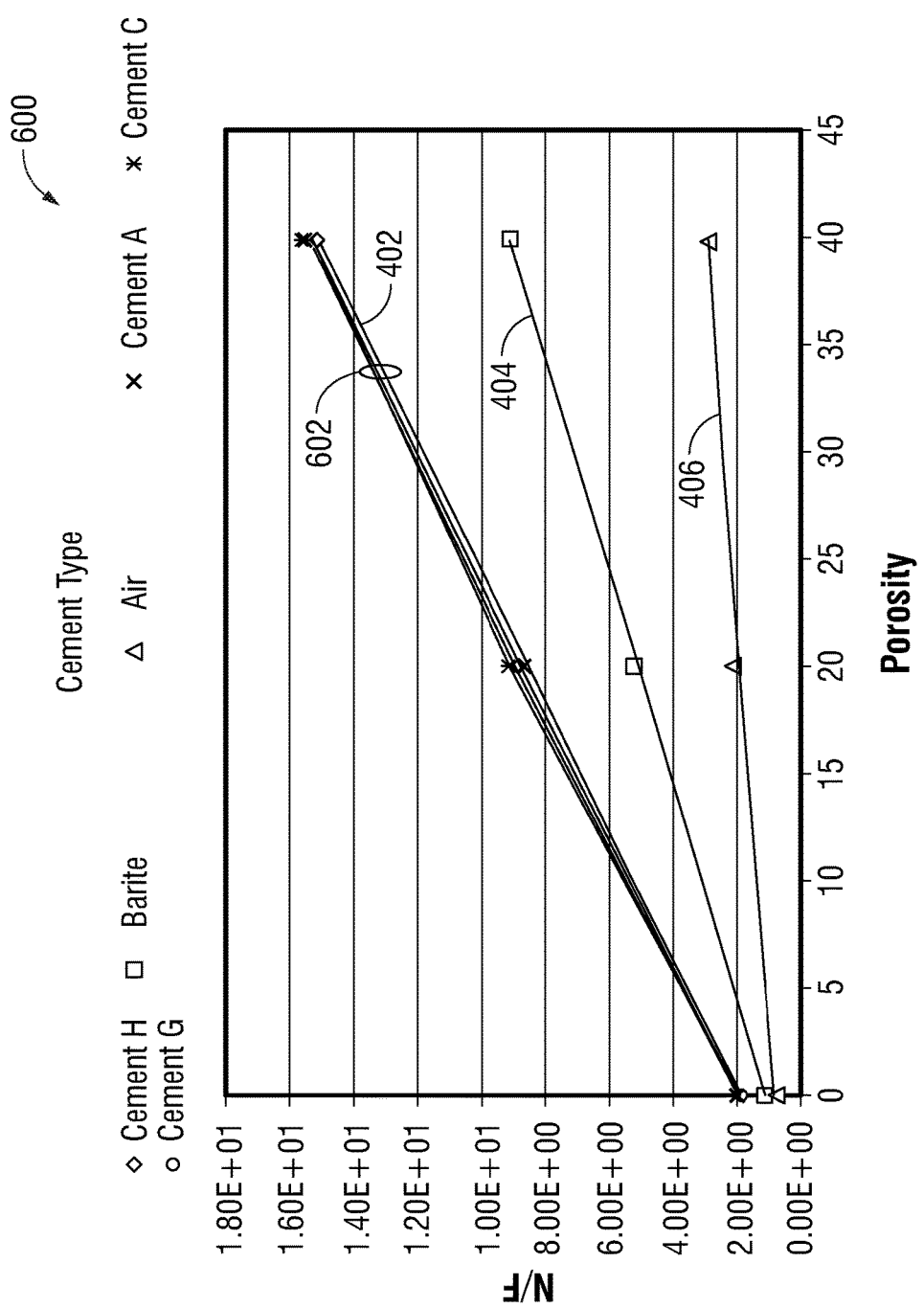
FIG. 6 illustrates exemplary neutron near-to-far ratios for materials in the annular space of yet another well according to the disclosed embodiments.

FIG. 6 shows an exemplary plot 600 in which the same N/F neutron count ratio curve 402, 404, 406 from FIG. 4 has been overlaid with data representing additional cement types "A,", "C," and "G," respectively. Again, because the data is clustered so closely, none of the curves representing the additional cement types has been separately labeled for ease of viewing. But as the figure shows, the N/F neutron count ratios for the different cement types also remain uniquely identifiable from the ratios for barite and air, assuming other downhole conditions stay the same.

Figure 7:
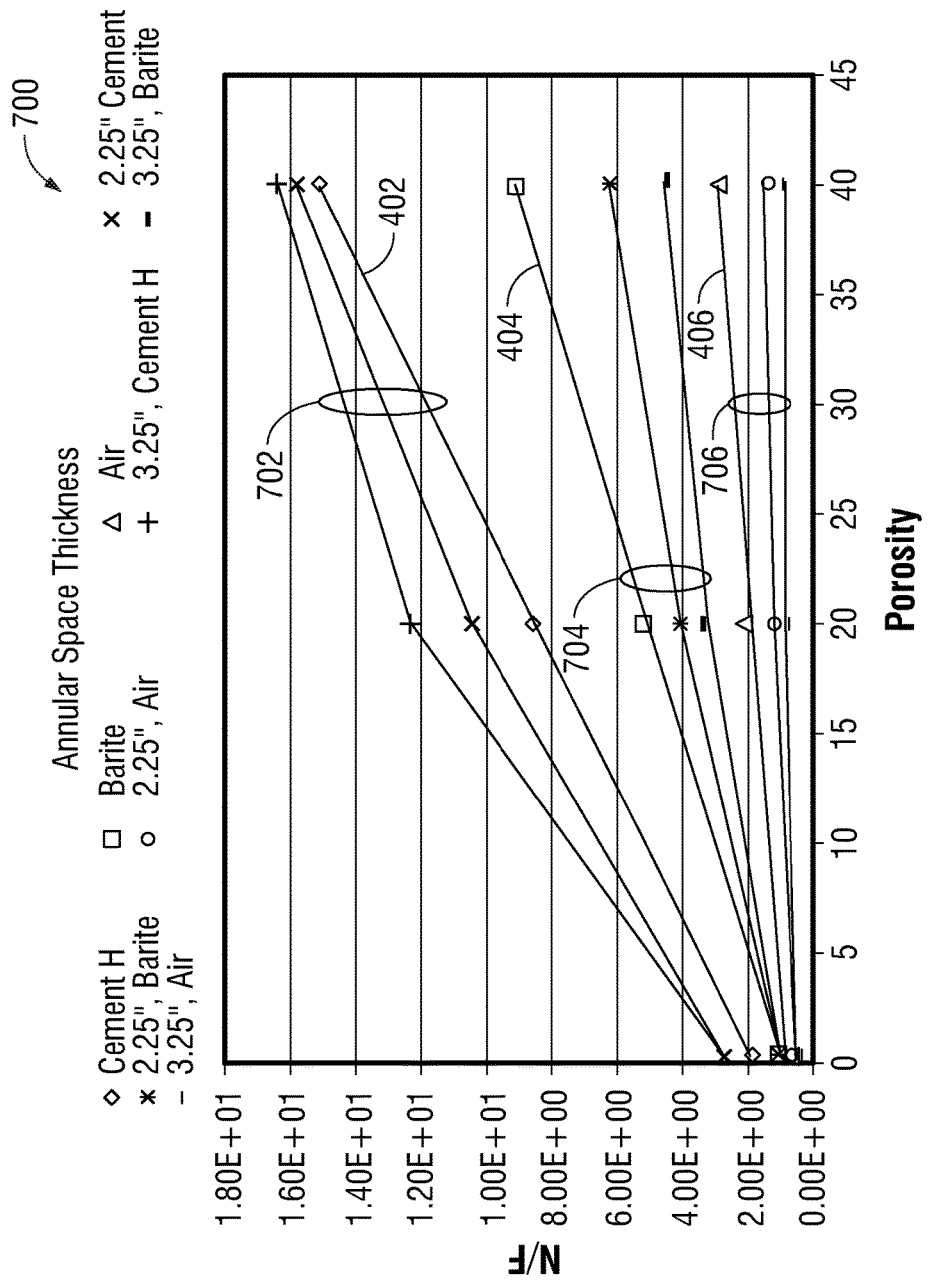
FIG. 7 illustrates exemplary neutron near-to-far ratios for materials in the annular space of still another well according to the disclosed embodiments.

FIG. 7 shows an exemplary plot 700 in which the same N/F neutron count ratio curve 402, 404, 406 from FIG. 4 has been overlaid with data representing larger annular spaces that measure about 2.25 inches thick and 3.25 inches thick, respectively. As this figure shows, the N/F neutron count ratios for cement, barite, and air at the larger annular space thicknesses respectively remain uniquely identifiable from one another, assuming other downhole conditions stay the same.

Accordingly, as FIGS. 4-7 show, the ability to differentiate among the three materials remains mostly unambiguous even when certain downhole conditions depart from the reference conditions, assuming other downhole conditions remain the same. More specifically, even when temperature, cement type, and annular space thickness vary, the N/F neutron count ratios for cement, barite, and air remain uniquely identifiable from one another. This is particularly useful, for example, where a well is drilled with a certain bit size, but the hole is washed out in some places so that the annular space thickness changes. Despite the change, the embodiments disclosed herein are still able to largely unambiguously identify the materials within the annular space.

It should of course be understood that the exemplary reference cases shown in this disclosure are not universally applicable. For practical purposes, a customized reference case would be generated for each well that corresponds to the nominal logging conditions of that particular well. This may be important because a customized reference case can in some instances significantly increase the ability of the material identification tool 218 to identify the different materials. For example, when the annular space between the casing and formation increases such that cement thickness also increases, FIG. 7 shows that a customized reference case could provide greater resolution among the three different materials. Such customization may include not only the three porosities (e.g., 0, 20, and 40) simulated in the figures, but also several additional porosity values as well.

Figure 8:
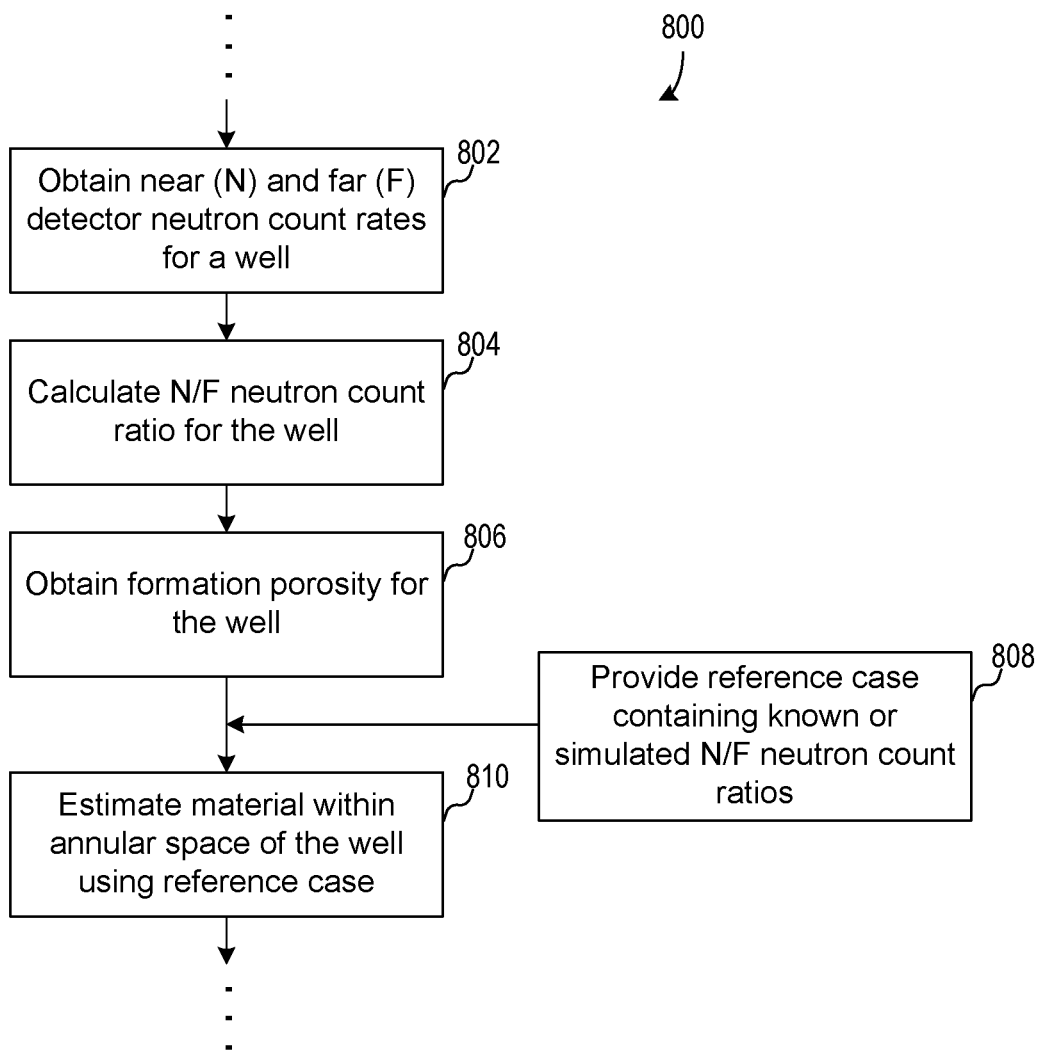
FIG. 8 illustrates an exemplary workflow that may be used with the material identification tool according to the disclosed embodiments.

Thus far, a number of specific implementations of a material identification tool have been described. Following now in FIG. 8 are general guidelines in the form of a flow chart 800, or portion thereof, outlining a method that may be used to implement the material identification tool. Those having ordinary skill in the art will understand of course that alternative arrangements may be derived from the teachings presented herein without departing from the scope of the disclosed embodiments.

As can be seen in FIG. 8, the flow chart 800, or portion thereof, begins at block 802 where neutron count rates are obtained for the well being investigated via a neutron logging tool having a neutron source. Specifically, the neutron count rates are obtained using at least one neutron detector positioned near to the neutron source and at least one neutron detector positioned far from the neutron source. Next, at block 804, a N/F neutron count ratio is calculated using the neutron count rates obtained by the at least one near neutron detector and the at least one far neutron detector. In some embodiments, the N/F neutron count ratio is calculated using Equation (1) above.

Thereafter, porosity information is obtained for the well at block 806 from previously obtained survey data or in real time as needed. A reference case containing simulated N/F neutron count ratios for different materials (e.g., cement, barite, air, etc.) under similar downhole conditions to the well being investigated may be provided at block 808. At block 810, the calculated N/F neutron count ratio is compared to the simulated N/F neutron count ratios from the reference case. If there is a match, then there is a high degree of confidence that the material filling the well annular space is substantially the same as the material represented by the matching N/F neutron count ratio.

Accordingly, as set forth above, the embodiments disclosed herein may be implemented in a number of ways. For example, in general, in one aspect, the disclosed embodiments relate to a system for identifying a material within an annular space of a well. The system comprises, among other things, a logging tool disposed within the well and having a neutron source coupled thereto, a first neutron detector disposed on the logging tool a first distance lengthwise from the neutron source, and a second neutron detector disposed on the logging tool a second distance lengthwise from the neutron source, the second distance being greater than the first distance. The system further comprises a material identification tool coupled to receive neutron count rates from the first neutron detector and the second neutron detector and operable to calculate a near-to-far neutron count ratio using the neutron count rates from the first neutron detector and the second neutron detector and identify the material within the annular space based on the near-to-far neutron count ratio.

In general, in another aspect, the disclosed embodiments relate to a method of identifying a material within an annular space of a well. The method comprises, among other things, the steps of lowering a logging tool having a neutron source coupled thereto into the well, detecting neutron count rates from a first neutron detector disposed on the logging tool a first distance lengthwise from the neutron source, and detecting neutron count rates from a second neutron detector disposed on the logging tool a second distance lengthwise from the neutron source, the second distance being greater than the first distance. The method further comprises calculating a near-to-far neutron count ratio using the neutron count rates from the first neutron detector and the second neutron detector and identifying the material within the annular space based on the near-to-far neutron count ratio.

In general, in yet another aspect, the disclosed embodiments relate to a computer-readable medium storing computer-readable instructions thereon for identifying a material within an annular space of a well. The computer-readable instructions cause a computing system to, among other things, receive neutron count rates detected by a first neutron detector disposed on a logging tool a first distance lengthwise from a neutron source thereof and receive neutron count rates detected by a second neutron detector disposed on the logging tool a second distance lengthwise from the neutron source, the second distance being greater than the first distance. The computer-readable instructions further cause a computing system to calculate a near-to-far neutron count ratio using the neutron count rates detected by the first neutron detector and the second neutron detector and identify the material within the annular space based on the near-to-far neutron count ratio.

In accordance with any of the foregoing embodiments, a formation porosity may be obtained for the well and the material within the annular space may be identified based on the formation porosity.

In accordance with any of the foregoing embodiments, a reference case may be obtained containing known or simulated near-to-far neutron count ratios and the material within the annular space may be identified based on the reference case.

In accordance with any of the foregoing embodiments, the material within the annular space may be identified as cement, barite, or air.

In accordance with any of the foregoing embodiments, the material within the annular space may be identified despite a temperature of the annular space being different from a reference annular space temperature.

In accordance with any of the foregoing embodiments, the material within the annular space may be identified despite a thickness of the annular space being different from a reference annular space thickness.

In accordance with any of the foregoing embodiments, the material within the annular space may be identified substantially in real time in situ.

While the invention has been described with reference to one or more particular embodiments, those skilled in the art will recognize that many changes may be made thereto without departing from the spirit and scope of the description. Each of these embodiments and obvious variations thereof is contemplated as falling within the spirit and scope of the claimed invention, which is set forth in the following claims.

What is claimed is:
1. A system for identifying a material within an annular space of a well, comprising:
   a logging tool disposed within the well, the logging tool having a neutron source coupled thereto;
   a first neutron detector disposed on the logging tool a first distance lengthwise from the neutron source;

a second neutron detector disposed on the logging tool a second distance lengthwise from the neutron source, the second distance being greater than the first distance; and a material identification tool coupled to receive neutron count rates from the first neutron detector and the second neutron detector, the material identification tool operable to calculate a near-to-far neutron count ratio using the neutron count rates from the first neutron detector and the second neutron detector and to identify the material within the annular space based on the near-to-far neutron count ratio;

wherein the material identification tool is further operable to identify the material within the annular space based on a customized reference case of near-to-far neutron count ratios that is unique to the nominal logging conditions of a particular well and is determined based on the dimensions of the annular space between the casing and the formation in the well.

2. The system of claim 1, wherein the material identification tool is further operable to obtain a formation porosity for the well and identify the material within the annular space based on the formation porosity.

3. The system of claim 1, wherein the material identification tool is further operable to identify the material within the annular space despite a temperature of the annular space being different from a reference annular space temperature.

4. The system of claim 1, wherein the material identification tool is further operable to identify the material within the annular space substantially in real time in situ.

5. A method of identifying a material within an annular space of a well, comprising:

lowering a logging tool into the well, the logging tool having a neutron source coupled thereto;

detecting neutron count rates from a first neutron detector disposed on the logging tool a first distance lengthwise from the neutron source;

detecting neutron count rates from a second neutron detector disposed on the logging tool a second distance lengthwise from the neutron source, the second distance being greater than the first distance;

calculating a near-to-far neutron count ratio using the neutron count rates from the first neutron detector and the second neutron detector; and identifying the material within the annular space based on the near-to-far neutron count ratio wherein the step of identifying the material the material within the annular space further comprises identifying the material within the annular space based on a customized reference case of near-to-far neutron count ratios that is unique to the nominal logging conditions of a particular well and is based on the dimensions of the annular space between the casing and the formation in the well.

6. The method of claim 5, further comprising obtaining a formation porosity for the well and identifying the material within the annular space based on the formation porosity.

7. The method of claim 6, wherein the material within the annular space is identified as cement, barite, or air.

8. The method of claim 5, wherein the material within the annular space is identified despite a temperature of the annular space being different from a reference annular space temperature.

9. The method of claim 5, wherein the material within the annular space is identified substantially in real time in situ.

10. A non-transitory computer-readable medium storing computer-readable instructions for identifying a material within an annular space of a well, the computer-readable instructions causing a computing system to:

receive neutron count rates detected by a first neutron detector disposed on the logging tool a first distance lengthwise from the neutron source;

receive neutron count rates detected by a second neutron detector disposed on the logging tool a second distance lengthwise from the neutron source, the second distance being greater than the first distance;

calculate a near-to-far neutron count ratio using the neutron count rates detected by the first neutron detector and the second neutron detector; and identify the material within the annular space based on the near-to-far neutron count ratio;

wherein the material is identified based on a customized reference case of near-to-far neutron count ratios that is unique to the nominal logging conditions of a particular well and is determined based on the dimensions of the annular space between the casing and the formation in the well.

11. The non-transitory computer-readable medium of claim 10, further comprising computer-readable instructions for causing the computing system to receive a formation porosity for the well and identify the material within the annular space based on the formation porosity.

12. The non-transitory computer-readable medium of claim 10, further comprising computer-readable instructions for causing the computing system to identify the material within the annular space as one of: cement, barite, or air.

13. The non-transitory computer-readable medium of claim 10, further comprising computer-readable instructions for causing the computing system to identify the material within the annular space despite a temperature of the annular space being different from a reference annular space temperature and despite a thickness of the annular space being different from a reference annular space thickness.

14. The non-transitory computer-readable medium of claim 10, further comprising computer-readable instructions for causing the computing system to identify the material within the annular space substantially in real time in situ.

* * * * *